United States Patent [19]

Takanohashi et al.

[11] Patent Number: 4,755,598
[45] Date of Patent: Jul. 5, 1988

[54] 1'-(SUBSTITUTED)ETHYL-7β-[2-(2-AMINO-THIAZOL-4-YL)ACETAMIDO]-3-[[[1-(2-DIMETHYLAMINOETHYL)-1H-TETRAZOL-5-YL]THIO]METHYL]CEPH-3-EM-4-CARBOXYLATE DERIVATIVES HAVING ANTIBACTERIAL UTILITY

[75] Inventors: Kunio Takanohashi, Kawanishi; Tomoyuki Fujii; Mitsuo Numata, both of Osaka, all of Japan

[73] Assignee: Takeda Chemical Industries, Ltd., Osaka, Japan

[21] Appl. No.: 616,260

[22] Filed: Jun. 1, 1984

[30] Foreign Application Priority Data

Jun. 2, 1983 [JP] Japan .................. 58-99211

[51] Int. Cl.$^4$ .................. C07D 501/36; A61K 31/545
[52] U.S. Cl. .................................................. 540/227
[58] Field of Search .................. 544/27, 227; 540/227

[56] References Cited

U.S. PATENT DOCUMENTS

| | | | |
|---|---|---|---|
| 3,935,204 | 1/1976 | Dahlen et al. | 544/27 |
| 4,080,498 | 3/1978 | Numata et al. | 544/27 |
| 4,189,479 | 2/1980 | Kakeya et al. | 544/27 |
| 4,497,809 | 2/1985 | Yoshimura et al. | 544/27 |

OTHER PUBLICATIONS

Nakao et al., "7 Methoxycephalosporine Compounds . . . ," Chem. Abst. 92:146752(t), 1980.
Takahashi et al., ". . . Cephalosporanates," Chem. Abst. 78:124612(f) 1973.
Takahashi, et al., ". . . Desacetoxy Cephalosporanates," Chem. Abst. 78:124613(g) 1973.
Takahashi et al., ". . . Cephalosporanates," Chem. Abst. 78:111337(v) 1972.

Takeda Ind., Chem. Abstracts vol. 97 (1982), entry 144673x.

*Primary Examiner*—Mark L. Berch
*Assistant Examiner*—William A. Teoli, Jr.
*Attorney, Agent, or Firm*—Antonelli, Terry & Wands

[57] ABSTRACT

A compound of the formula:

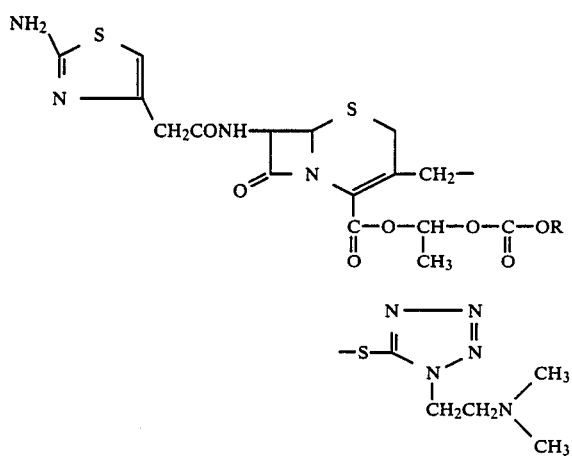

wherein R is 2-methylpropyl, 2,2-dimethylpropyl, 1-ethylpropyl, 1-methylbutyl, 2-methylbutyl, 3-methylbutyl, n-pentyl, an alkyl group of 6 or 7 carbon atoms, or an alkenyl group of 2 to 7 carbon atoms, or a pharmaceutically acceptable salt thereof and processes for preparing the same are provided. The compound can orally be applied as antibiotics having improved absorbability.

3 Claims, No Drawings

1'-(SUBSTITUTED)ETHYL-7β-[2-(2-AMINO-THIAZOL-4-YL)ACETAMIDO]-3-[[[1-(2-DIMETHYLAMINOETHYL)-1H-TETRAZOL-5-YL]THIO]METHYL]CEPH-3-EM-4-CARBOXYLATE DERIVATIVES HAVING ANTIBACTERIAL UTILITY

This invention relates to compounds of the formula

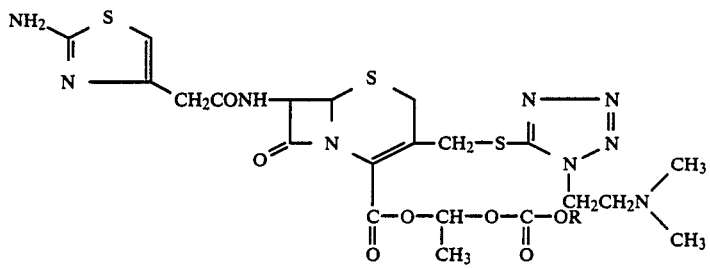

[wherein R is 2-methylpropyl, 2,2-dimethylpropyl, 1-ethylpropyl, 1-methylbutyl, 2-methylbutyl, 3-methylbutyl, n-pentyl, an alkyl group of 6 or 7 carbon atoms, or an alkenyl group of 2 to 7 carbon atoms] or pharmaceutically acceptable salts thereof.

For the purpose of promoting absorption, on oral administration, of the non-ester form of the compound [I], i.e. 7β-[2-(2-aminothiazol-4-yl)acetamido]-3-[[[1-(2-dimethylaminoethyl]-1H-tetrazol-5-yl]thio]methyl]-ceph-3-em-4-carboxylic acid (common name: cefotiam; hereinafter referred to briefly as compound [II]; described in U.S. Pat. No. 4,080,498), it has been suggested to esterify its 4-carboxyl group into, for example, a pivaloyloxymethyl ester (U.S. Pat. No. 4,189,479 and Japanese Published Unexamined Patent Application No. 77690/1982).

However, this ester as well as other esters so far proposed are not fully satisfactory in absorption rate, stability, etc.

The present inventors explored a variety of derivatives of the compound [II] which might exhibit more favorable absorption characteristics on oral administration and greater stability and found that the above compound [I] [referred to briefly as the ester] is well absorbed from the gastrointestinal tract and gives rise to said non-ester compound [II] in the body promptly after absorption to give a high concentration of [II] in the blood and is, therefore, a useful orally administrable broad-spectrum antibiotic which exhibits strong activity not only against gram-positive and gram-negative bacteria, but also against resistant strains thereof and that the compound [I], when made available in the form of a suitable salt, offers greater water-solubility and better absorption rate and facilitates the procedures of isolation, stabilization and processing into pharmaceutical preparations. This invention is predicated on the above findings.

Referring to the above formula [I], R is 2-methylpropyl, 2,2-dimethylpropyl, 1-ethylpropyl, 1-methylbutyl, 2-methylbutyl, 3-methylbutyl, n-pentyl, a straight-chain or branched alkyl group of 6 to 7 carbon atoms such as n-hexyl, 1-methylpentyl, 2-methylpentyl, 3-methylpentyl, 4-methylpentyl, 1-ethylbutyl, 2-ethylbutyl, 3-ethylbutyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl and 1-propylbutyl, etc., or a straight-chain or branched alkenyl group of 2 to 7 carbon atoms which may contain 1 to 3 unsaturated bond such as vinyl, allyl, 1-propenyl, 1-methyl-1-propenyl, 2-methyl-1-propenyl, 1-butenyl, 2-butenyl, 3-butenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1-pentenyl, 2-pentenyl, 3-pentenyl, 4-pentenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1-hexenyl, 1-methyl-1-hexenyl, 2-methyl-1-hexenyl, 3-methyl-1-hexenyl, 4-methyl-1-hexenyl, 5-methyl-1-hexenyl, 1-methyl-2-hexenyl, 2-methyl-2-hexenyl, 3-methyl-2-hexenyl, 4-methyl-2-hexenyl, 5-methyl-2-hexenyl, 1-methyl-3-hexenyl, 2-methyl-3-hexenyl, 3-methyl-3-hexenyl, 4-methyl-3-hexenyl, 5-methyl-3-hexenyl, 1-methyl-4-hexenyl, 2-methyl-4-hexenyl, 3-methyl-4-hexenyl, 4-methyl-4-hexenyl, 5-methyl-4-hexenyl, 1,3-butanedienyl, 1,3-pentanedienyl, 1,4-pentanedienyl, 1,3-hexanedienyl, 1,4-hexanedienyl, 1,5-hexanedienyl, 1,3-dimethyl-1,3-butanedienyl, 1-methyl-1,3-pentanedienyl, 3-methyl-1,3-pentanedienyl, 1-methyl-1,4-pentanedienyl, 4-methyl-1,4-pentanedienyl, 1-methyl-1,3-hexanedienyl, 3-methyl-1,3-hexanedienyl, 1-methyl-1,4-hexanedienyl, 4-methyl-1,4-hexanedienyl, 1-methyl-1,5-hexanedienyl, 5-methyl-1,5-hexanedienyl, 1,3-heptanedienyl, 1,4-heptanedienyl, 1,5-heptanedienyl and 1,6-heptanedienyl.

Among the above-mentioned groups, preferred species of R are 1-methylbutyl, 3-methylbutyl, 2-ethylbutyl, 2,2-dimethylpropyl and 2-methylpentyl.

More preferably, R is 2-methylpropyl, 2,2-dimethylpropyl, 1-methylbutyl, 1-ethylpropyl, 3-methylbutyl, n-pentyl, 2-ethylbutyl or 2-methylpentyl.

Being basic as it is, the compound [I] is capable of forming an acid addition salt.

Nontoxic acids which are usually employed for the formation of such acid addition such include those known to form pharmaceutically acceptable salts of penicillins and cephalosporins, for example inorganic acids such as hydrochloric acid, sulfuric acid, phosphoric acid, etc. and organic acids such as maleic acid, acetic acid, citric acid, succinic acid, tartaric acid, malic acid, malonic acid, fumaric acid, benzoic acid, mandelic acid, ascorbic acid, methanesulfonic acid, etc. Preferred salts of the compound [I] are the corresponding monohydrochloride and dihydrochloride. The most desirable is the dihydrochloride. The aminothiazole group of the compound [I] may exist in the tautomeric form of iminothiazoline.

As the compound [I] or a salt thereof has an asymmetric carbon in the carboxyl ester group at 4-position of the cephem nucleus, there exist two optically active forms (D-isomer and L-isomer). The compound [I] or a salt thereof can generally be used as a racemic compound but either the D-isomer or L-isomer or a mixture of such optical isomers can also be employed. The compound [I] or a salt thereof is absorbed well through the gastrointestinal tract and after absorption the ester moiety at its 4-carboxyl position is promptly hydrolyzed with enzyme in the body to give the non-ester form of compound [I], which is the compound [II].

The compound [II] has strong antibacterial activity as mentioned in Antimicrobial Agent and Chemotherapy 14, 557–568 (1978). Thus, the compound [II] displays potent antibacterial activity against gram-positive bacteria such as *Staphylococcus aureus*, etc. and gram-negative bacteria such as *Escherichia coli, Klebsiella pneumoniae, Proteus vulgaris, Proteus mirabilis* and *Proteus morganii*.

Since the compound [I] or a salt thereof, when administered by the oral route, gives a high concentration of the compound [II] in the blood, it is effective in the treatment of infections due to said bacteria in man and other mammalian animals, such as respiratory tract and urinary tract infections due to said bacteria.

The compound [I] or a salt thereof is low in toxicity ($LD_{50} \geq 3$ g/kg, mice, p.o.) and can be orally administered. Therefore, in combination with per se known parmaceutically acceptable excipients (e.g. starch, lactose, calcium carbonate, calcium phosphate, etc.), binders (e.g. starch, gum arabic, carboxymethylcellulose, hydroxypropylcellulose, crystalline cellulose, etc.), lubricants (e.g. magnesium stearate, talc, etc.) or/and disintegrating agents (e.g. carboxymethylcalcium, talc, etc.), the compound [I] or a salt thereof can be formulated into such dosage forms as capsules, powders, fine granules, granules, tablets, etc. It is also possible to add about 1 to 5 mole equivalents of a solid organic acid (e.g. citric acid, malic acid, tartaric acid, succinic acid, ascorbic acid, mandelic acid, etc.) to the compound [I] or a salt thereof and mold the mixture into granules in a conventional manner. Such granules can be further processed into capsules, tablets, etc. by the established pharmaceutical procedures.

With regard to the dosage regimen, the compound [I] or a salt thereof can be administered at a daily dose of 0.3 to 5 g per adult human, preferably 0.5 to 3 g per adult human, divided into 3 or 4 equal doses.

The compound [I] or a salt thereof can be produced by per se known processes (for example, the processes described in the specifications of U.S. Pat. Nos. 4,080,498, 4,189,479 and Japanese Published Unexamined Patent Application No. 77690/1982). Moreover, the compound [I] or a salt thereof can be produced by esterifying the compound [II] or a salt thereof with a compound of the formula:

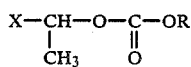

[III]

[wherein X is a halogen atom; R has the same meaning as defined hereinbefore].

Referring to the above formula [III], the halogen atom represented by X is, for example, chlorine, bromine and iodine. Of these species, X is preferably iodine for the purpose of esterification.

As the compound [III] has an asymmetric carbon atom, it can be optically resolved into D- and L-isomers by a per se known procedure and either of the isomers or a mixture thereof can be used in the contemplated esterification reaction. The starting compound [II] can be subjected to the reaction in the form of an acid addition salt with an organic acid such as hydrochloric acid, sulfuric acid and nitric acid, or an organic acid such as oxalic acid and p-toluenesulfonic acid or in the form of a salt with a base such as an alkali metal, e.g. sodium, potassium, etc., an alkaline earth metal, e.g. calcium, magnesium, etc., and an organic amine, e.g. triethylamine, trimethylamine, pyridine, collidine, lutidine, etc.

In the esterification reaction, the starting compound [III] is used in a proportion of about 1 to 3 mole equivalents to each equivalent of the starting compound [II] or a salt thereof.

This reaction is generally carried out in a solvent inert to the reaction. Suitable species of such solvent include amides such as N,N-dimethylformamide (hereinafter referred to briefly as DMF), N,N-dimethylacetamide (hereinafter referred to briefly as DMAC), hexamethylphosphorotriamide (hereinafter referred to briefly as HMPA), etc., halogenated hydrocarbons such as dichloromethane, chloroform, etc., sulfoxides such as dimethyl sulfoxide (hereinafter referred to briefly as DMSO), sulfolane, etc., ethers such as dioxane, tetrahydrofuran (hereinafter referred to briefly as THF), ketones such as acetone, methyl ethyl ketone, etc., nitriles such as acetonitrile, etc., liquefied sulfur dioxide, and so forth. Preferred are DMF, DMAC, HMPA, acetone, acetonitrile, liquefied sulfur dioxide, etc. This esterification reaction is conducted generally at a temperature between about $-20°$ C. and $20°$ C. While the reaction can be conducted in the absence of a catalyst, a catalyst such as a phase transfer catalyst (e.g. 18-crown-6, etc.) can be employed. When liquefied sulfur dioxide is used as the solvent, the reaction is preferably conducted at a temperature near the boiling point ($-10°$ C.) of the solvent, i.e. $-10°$ C. to $-20°$ C. The reaction time is generally several minutes to about 1 hour, depending on the species of reactants and solvent, etc.

The compound [I] or a salt thereof can also be produced by the following processes. Thus, a compound of the formula:

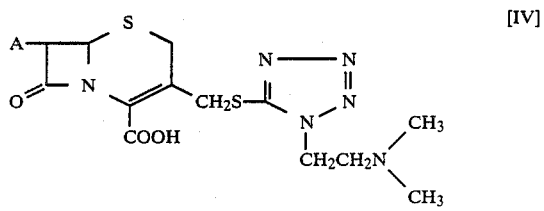

[IV]

[wherein A is an amino group or an acylamino group other than 2-(2-aminothiazol-4-yl)acetylamino] is reacted with the compound [III] in the same manner as the above-described esterification reaction and when A is an acylamino group, the resulting ester compound is reacted with phosphorus pentachloride and, then, with alcohol (e.g. methanol, ethanol, propanol, isopropyl alcohol, n-butanol, etc.) [the process described in Journal of Medicinal Chemistry 18, 992 (1975), and West German Laid-open Patent Application Nos. 2460331 and 2460332]. The resulting compound of the formula:

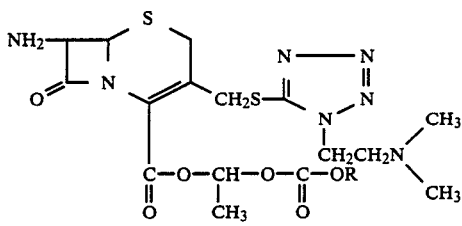

[wherein symbols have the same meanings as defined hereinbefore] or a salt thereof is acylated with 2-(2-aminothiazol-4-yl)acetic acid of the formula:

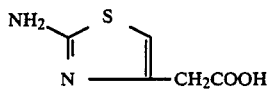

or a reactive derivative thereof, to give the compound [I] or a salt thereof.

Referring to the above formula [IV], when A is an acylamino group, the acyl group can be any of the acyl groups known per se in the field of cephalosporin compounds. Preferred species of such acylamino group are acetylamino, benzoylamino, phenylacetylamino, thienylacetylamino, phenyloxyacetylamino, and 5-amino-5-carboxyvalerylamino (the substituent amino group may be protected with phthaloyl or the like). When A is an amino group or an amino-substituted acylamino group, the substituent amino group is preferably protected before the reaction and the protective group therefor may for example be per se known protective groups for an amino group such as t-butoxycarbonyl, carboxybenzyloxy, 2-hydroxy-1-naphthocarbonyl, trichloroethoxycarbonyl, 2-ethoxycarbonyl-1-methylvinyl and 2-methoxycarbonyl-1-methylvinyl.

The deacylation of the ester compound produced by reacting compound [IV] (when A is an acylamino group) with the compound [III] is conducted in a per se known manner, using generally about 2 to 5 mole equivalents of phosphorus pentachloride and about 10 to 40 mole equivalents of alcohol per mole of the starting ester compound. This reaction is generally conducted in an inert solvent such as halogenated hydrocarbons, e.g. dichloromethane, chloroform, etc. For the purpose of accelerating the reaction, a tertiary amine such as triethylamine, pyridine, N,N-dimethylaniline may be added to the reaction system. The reaction temperature is about −40° C. to about −20° C. The reaction time is usually about 1 hour.

When the resulting compound [V] or a salt thereof is reacted with the compound [VI] or a reactive derivative thereof to produce the compound [I] or a salt thereof, the amino group of the compound [VI] is preferably protected beforehand and the protective group can be similar to the protective group for the amino group of the compound [IV]. In this reaction, the compound [VI] may be used in the form of its reactive derivative. Thus, for example, it is subjected to said acylation reaction in the form of the reactive derivative such as the corresponding acid halides, acid anhydrides, mixed acid anhydrides, active amides, active esters, etc. Preferred are the active esters, mixed acid anhydrides, acid halides, etc. Examples of such active esters are p-nitrophenyl ester, 2,4-dinitrophenyl ester, 2-mercaptobenzothiazole ester, pentachlorophenyl ester, N-hydroxyphthalimide ester, and the ester formed by means of a Vilsmeier or similar reagent, and so on. The mixed acid anhydries are those prepared from carbonic monoesters such as monomethyl carbonate, monoisobutyl carbonate, etc., and those prepared from lower alkanoic acids of 2 to 5 carbon atoms which may be substituted by halogens, such as pivalic acid, trichloroacetic acid, etc. Examples of such acid halides are acid chloride, acid bromide, etc. In this reaction, the compound [VI] or a reactive derivative thereof is used in a proportion of about 1 to 2 mole equivalents to each mole equivalent of the compound [V] or a salt thereof.

When the compound [VI] is used in the form of free acid or a salt thereof, a suitable condensing agent is employed. Examples of such suitable condensing agent include N,N'-di-substituted carbodiimides such as N,N'-dicyclohexylcarbodiimide, azolides such as N,N'-carbonylimidazole, N,N'-thionyldiimidazole, etc., and such dehydrating agents as N-ethoxycarbonyl-2-ethoxy-1,2-dihydroquinoline, phosphorus oxychloride, alkoxyacetylenes (e.g. ethoxyacetylene) and so on. When such a condensing agent is employed, the reaction appears to proceed via formation of a reactive derivative of the carboxylic acid.

Generally, this reaction can be smoothly conducted in a solvent. Examples of the solvent include the common solvents which do not interfere with the reaction to produce the compound [I], such as water, acetone, diisobutyl ketone, THF, ethyl acetate, dioxane, acetonitrile, chloroform, dichloromethane, dichloroethylene, pyridine, dimethylaniline, DMF, DMAC, DMSO, etc., as well as mixtures of such solvents. While the reaction temperature is virtually optional, the reaction is generally conducted under cooling or at room temperature. When the reaction proceeds with liberation of an acid, a base is added to the reaction system as necessary. The base used for this purpose is exemplified by aliphatic, aromatic or heterocyclic nitrogen-containing bases such as triethylamine, N,N-dimethylaniline, N-ethylmorpholine, pyridine, collidine, 2,6-lutidine, etc., alkali metal carbonates such as sodium carbonate, potassium carbonate, etc., and alkali metal bicarbonates such as potassium hydrogen carbonate, sodium hydrogen carbonate, etc. When the acylation reaction proceeds dehydratingly, it is preferable to remove water from the solvent. In some instances, the reaction is conducted under moisture-free conditions, e.g. in an inert gaseous atmosphere such as nitrogen gas. When the reaction product has a protective group, the protective group is removed by a per se known procedure.

The compound [I] or a salt thereof can also be produced by the following procedure. Thus, the compound [V] is reacted with a 4-halo-3-oxobutyryl halide, which is obtained by reacting diketene with a halogen (e.g. chlorine or bromine) in an equimolar ratio, to give a compound of the formula:

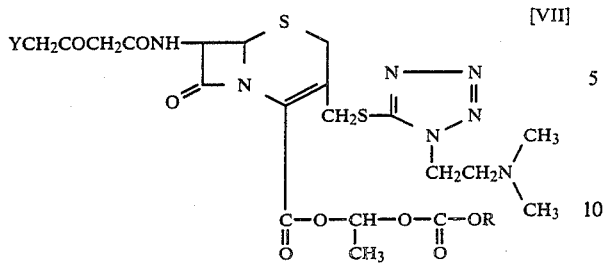

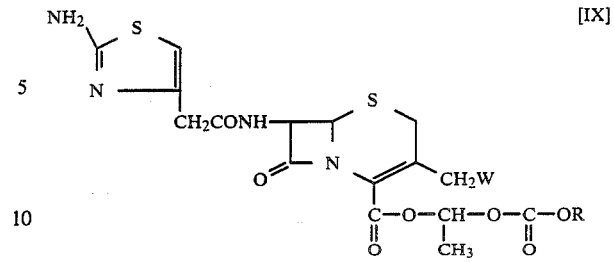

[wherein Y is a halogen atom and R has the same meaning as defined hereinbefore], which is then reacted with thiourea. In the above formula [VII], the halogen atom Y is, for example, chlorine, bromine and iodine.

In reaction of the compound [VII], with thiourea, thiourea is preferably used as it is but may be used in the form of a salt with an alkali metal such as lithium, sodium and potassium, or in the form of ammonium salt. Generally the reaction is carried out using the two reactants in an equimolar ratio in a solvent and, in some instances, can be conducted in the presence of 1 to 2 molar equivalents of a base if necessary. Preferred examples of said solvent include water, methanol, ethanol, acetone, dioxane, acetonitrile, chloroform, ethylene chloride, THF, ethyl acetate, DMF, DMAC, DMSO, etc. Among these solvents, hydrophilic solvents can be used in admixture with water. Preferred examples of said base include alkali metal hydroxides such as sodium hydroxide, potassium hydroxide, etc., alkali metal carbonates such as sodium carbonate, potassium carbonate, etc., alkali metal hydrogen carbonates such as sodium hydrogen carbonate, etc., and organic tertiary amines such as triethylamine, trimethylamine, pyridine etc. While there is virtually no limitation on the reaction temperature, generally the reaction is preferably conducted under cooling. The reaction generally proceeds at a fast rate and goes to completion within 10 minutes, although a reaction time in excess of 30 minutes is at times required. The compound [VII] can be easily produced by the above-described process or other processes known per se.

The compound [I] or a salt thereof can also be produced by reacting a compound of the formula:

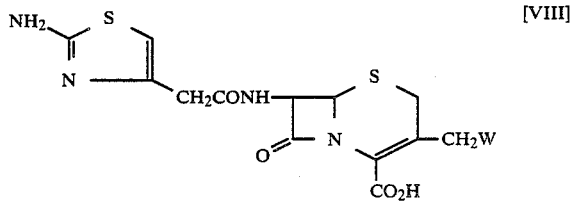

[wherein W is acetoxy, acetoacetoxy, a halogen atom or carbamoyloxy] or a salt thereof with the compound [III] in the same manner as the esterification reaction described hereinbefore and reacting the resulting compound of the formula:

[wherein symbols have the same meanings as defined hereinbefore] or a salt thereof with 1-(2-dimethylaminoethyl)-5-mercapto-1H-tetrazole. Referring to the above formulas [VIII] and [IX], the halogen atom represented by W is, for example, chlorine, bromine and iodine. In this reaction, the starting material 1-(2-dimethylaminoethyl)-5-mercapto-1H-tetrazole is used in an approximately equimolar proportion with respect to the compound [IX] or a salt thereof.

This reaction can generally be conducted smoothly in a solvent. Examples of such solvent include water, THF, ethyl acetate, dioxane, acetonitrile, chloroform, dichloromethane, DMF, DMAC, DMSO, etc. When water is used, it can be used in admixture with a highly water-miscible organic solvent. Generally, this reaction is conducted in the presence of a base. Preferred examples of the base are weak bases such as alkali metal carbonates (e.g. sodium carbonate, potassium carbonate etc.), alkali metal bicarbonates (e.g. sodium hydrogen carbonate, potassium hydrogen carbonate, etc.). The base is used in an approximately equimolar proportion with respect to the starting compound 1-(2-dimethylaminoethyl)-5-mercapto-1H-tetrazole. While the reaction temperature is more or less optional, the reaction is generally conducted at room temperature up to 40° C. through 60° C. The reaction time is about 30 minutes to about 3 hours, depending on the species of solvent and the reaction temperature.

If the compound [I] or a salt thereof prepared as above contains its $\Delta^2$-isomer, the isomer can be converted into the compound [I] or a salt thereof by, for example, isomerizing the isomer to the $\Delta^3$-isomer by a per se known method [Journal of Medicinal Chemistry, Vol. 18, 986 (1975)], or converting the isomer to the $\Delta^3$-isomer via a corresponding S-oxide derivative and reducing it.

When the compound [I] is produced in the form of free base, it can be converted to a salt thereof by dissolving it in an inert solvent such as dichloromethane and chloroform, and adding about 1 to 10 mole equivalents of an acid with respect to the compound [I] to the solution. When the compound [I] is produced in the form of an acid addition salt, it can be converted to the form of free base according to a per se known procedure. When the compound [I] or a salt thereof is produced in the form of a racemic mixture, it can be subjected to the optical resolution according to a known procedure per se to isolate the optically active compounds (D- and L-isomers). The resulting compound [I] or a salt thereof can be isolated and purified by per se known procedures such as solvent extraction, pH adjustment, solvent-transformation, crystallization, recrystallization and chromatography.

The starting compound [III] is produced by per se known processes. The compound [III] can also be produced by the process illustrated below.

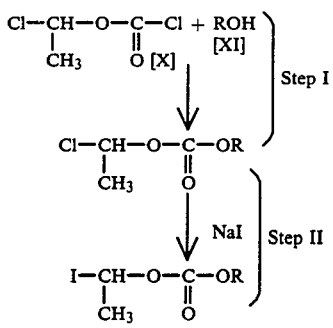

In the above formulas, R has the same meaning as defined hereinbefore.

The compound [X] can be produced according to the known method e.g. one described in EP No. 40153A or an analogous method thereto.

The compound [III] wherein X is iodine can be produced by reacting the compound [X] with the compound [XI] (Step I) and, then, further with sodium iodide (Step II).

The reaction of the compound [X] with the compound [XI] (Step I) is generally conducted in a solvent. Among suitable species of said solvent are an inert solvent to the reaction such as, halogenated hydrocarbons such as methylene chloride, chloroform, etc., nitriles such as acetonitrile, propionitrile, etc., amides such as N,N-dimethylformamide, N,N-dimethylacetamide, etc. This reaction gives rise to formation of hydrogen chloride. Therefore, the use of an acid acceptor such as an organic tertiary amine, e.g. pyridine and triethylamine, hastens the progress of the reaction. The reaction temperature is −20° C. to 100° C., preferably −10° C. to 40° C. The reaction goes to completion in about 1 to 5 hours.

The resulting compound [III] [wherein X is chlorine] is purified by the conventional isolation/purification procedure such as distillation and column chromatography. This compound is then reacted with sodium iodide to give the compound [III] [wherein X is iodine].

This reaction (Step II) is conducted in the presence of the common solvent such as acetone, acetonitrile, N,N-dimethylformamide, dimethyl sulfoxide, etc. The reaction temperature may be room temperature up to about 80° C. The reaction time is 15 minutes to about 6 hours, preferably about 15 minutes to about 2 hours. The reaction product can be isolated and purified by the per se known procedures such as solvent extraction, pH adjustment, solvent transformation, extraction, crystallization, chromatography, etc.

The compound [X] is produced in the form of a racemic mixture according to the method described in EP No. 40153A or Reference Example 1 of the present invention.

When the compound [X] in the form of a racemic mixture is subjected to the following reaction, the resulting compound [III] (wherein X is chlorine or iodine) is also produced in the form of racemic mixture.

The following examples are given to illustrate the present invention more precisely.

In Reference Examples and Examples, the used symbols have the following meanings:

s: singlet
d: doublet
t: triplet
q: quartet
AB-q: AB-type quartet
m: multiplet
quin: quintet
J: coupling constant
bp: boiling point
b: broad

REFERENCE EXAMPLE 1

1-Chloroethyl chloroformate

Chlorine (500 g) is bubbled into 300 ml of ethyl chloroformate over a period of 6 hours. After the vessel is tightly closed, the mixture is allowed to stand for a day. The reaction mixture is distilled at atmospheric pressure to give 187 g of 1-chloroethyl chloroformate, boiling at 126°–130° C./760 mm Hg.

NMR (CDCl$_3$, 60 MH$_z$)δ: 1.86(d, J=6 Hz, 3H), 6.45(q, J=6 Hz, 1H).

REFERENCE EXAMPLE 2

1-Iodoethyl 2-methylbutyl carbonate (a) 1-Chloroethyl 2-methylbutyl carbonate

In 70 ml of dichloromethane are dissolved 13 ml of 2-methyl-1-butanol and 17 g of 1-chloroethyl chloroformate, and the solution is cooled to 0° C. With stirring, a solution of 9.6 ml of pyridine in 30 ml of dichloromethane is added dropwise, and the mixture is stirred for 30 minutes. The salt precipitate is collected by filtration and the filtrate is washed with two 200-ml portions of water and dried over anhydrous sodium sulfate. The solvent is then distilled off under reduced pressure and the residue is further distilled under reduced pressure to give 12.5 g of 1-chloroethyl 2-methylbutyl carbonate.

bp 104°–106° C./20 mmHg.
IR (liquid film)cm$^{-1}$: 1765.
NMR(CDCl$_3$, 60 MHz) δ: 0.92(t, J=6 Hz, 3H), 0.96(d, J=6 Hz, 3H), 1.00–1.80(m, 3H), 1.85(d, J=6 Hz, 3H), 4.06(d, J=6 Hz, 2H), 6.45(q, J=6 Hz, 1H).

(b) 1-Iodoethyl 2-methylbutyl carbonate

To 250 ml of acetonitrile warmed to 50° C. is added 30 g of sodium iodide. To the resulting solution is added 10 g of 1-chloroethyl 2-methylbutyl carbonate. The mixture is stirred for 2 hours, poured into 250 ml of ice-water and extracted with two 200-ml portions of ethyl acetate. The organic layer is washed with 150 ml of 5% aqueous sodium thiosulfate, 300 ml of water and two 300-ml portions of saturated aqueous sodium chloride in that order and dried over anhydrous sodium sulfate. The solvent is then distilled off under reduced pressure to give 10.7 g of an approximately 1:1 mixture of 1-iodoethyl 2-methylbutyl carbonate and 1-chloroethyl 2-methylbutyl crarbonate.

NMR(CDCl$_3$, 60 MHz) δ: 2.25(d, J=6 Hz, 3H, 6.76(t, J=6 Hz, 1H).

Several compounds produced by the procedure of Reference Example 2 (a) are listed below together with their physico-chemical constants.

1-chloroethyl 3-methylbutyl carbonate bp 120°–122° C./30 mmHg.
NMR(CDCl$_3$, 60 MHz)δ: 0.94(d, J=6 Hz, 6H), 1.25–1.90(m, 3H), 1.84(d, J=6 Hz, 3H), 4.23(t, J=7 Hz, 2H), 6.44 (q, J=6 Hz, 1H).

1-chloroethyl 2-ethylbutyl carbonate bp 129°–132° C./34 mmHg.
NMR(CDCl₃, 60 MHz)δ: 0.90(t, J=6 Hz, 6H), 1.10–1.80 (m, 5H), 1.83(d, J=6 Hz, 3H), 4.12(d, J=6 Hz, 2H), 6.44(q, J=6 Hz, 1H).

1-chloroethyl 2-methylpropyl carbonate bp 102°–105° C./35 mmHg.
NMR(CDCl₃, 60 MHz)δ: 0.96(d, J=6 Hz, 6H), 1.84(d, J=6 Hz, 3H), 1.80–2.30(m, 1H), 3.98(d, J=6 Hz, 2H), 6.45 (q, J=6 Hz, 1H).

1-chloroethyl 2-methylpentyl carbonate bp 116°–118° C./27 mmHg.
NMR(CDCl₃, 60 MHz)δ: 0.9(t, J=6 Hz, 3H), 0.95(d, J=6 Hz, 3H), 1.0–1.8(m, 5H), 1.84(d, J=6 Hz, 3H), 4.05(d, J=6 Hz, 2H), 6.45(q, J=6 Hz, 1H).

1-chloroethyl 2,2-dimethylpropyl carbonate bp 107°–110° C./32 mmHg.
NMR(CDCl₃, 60 MHz)δ: 1.0(s, 9H), 1.85(d, J=6 Hz, 3H), 6.45(q, J=6 Hz, 1H), 3.92(s, 2H).

1-chloroethyl 2-pentyl carbonate bp 116°–120° C./30 mmHg.
NMR(CDCl₃, 60 MHz)δ: 0.7–1.1(t, J=6 Hz, 3H), 1.0–1.8(m, 5H), 1.31(d, J=6 Hz, 3H), 1.84(d, J=6 Hz, 3H), 4.65–5.10(m, 1H), 6.44(q, J=6 Hz, 1H).

1-chloroethyl 3-methyl-3-butenyl carbonate bp 121°–124° C./30 mmHg.
NMR(CDCl₃, 60 MHz)δ: 1.78(s, 3H), 1.84(d, J=6 Hz, 3H), 2.4(t, J=6 Hz, 2H), 4.3(t, J=6 Hz, 2H), 4.8(b-s, 2H), 6.44(q, J=6 Hz, 1H).

1-chloroethyl n-pentyl carbonate bp 105°–108° C./22 mmHg.
NMR(CDCl₃, 60 NHz)δ: 0.9(t, J=6 Hz, 3H), 1.0–1.8(m, 6H), 1.84(d, J=6 Hz, 3H), 4.17(t, J=7 Hz, 2H), 6.44(q, J=6 Hz, 1H).

1-chloroethyl 3-pentyl carbonate

NMR(CDCl₃, 60 MHz)δ: 0.93(t, J=7 Hz, 6H), 1.68(quin, J=6 Hz, 4H), 1.84(d, J=6 Hz, 3H), 4.65(quin, J=6 Hz, 1H), 6.40(q, J=6 Hz, 1H).

1-chloroethyl 2,4-dimethyl-3-pentyl carbonate

NMR(CDCl₃, 60 MHz)δ: 0.93(d, J=7 Hz, 12H), 1.84(d, 6 Hz, 3H), 1.0–2.9(m, 2H), 4.43(t, J=6 Hz, 1H), 6.40(q, J=6 Hz, 1H).

EXAMPLE 1

1-(2-Methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate In 80 ml of dimethylacetamide is dissolved 5.6 g of potassium 7β-[2-(2-aminothiazol-4-yl)acetamido]-3-[[[1-(2-dimethylaminoethyl)-1H-tetrazol-5-yl]thio]methyl]-ceph-3-em-4-carboxylate, and the solution is cooled to −5° C. With stirring, 4.8 g of 1-iodoethyl 2-methylbutyl carbonate is added at one stroke and stirring is continued for 5 minutes. The reaction mixture is poured into a mixture of 300 ml of ethyl acetate and 200 ml of ice-water and the organic layer is separated. The aqueous layer is extracted with 200 ml of ethyl acetate and these organic layers are combined, water with three 150-ml portions of ice water and three 150-ml portions of saturated aqueous sodium chloride in that order and dried over anhydrous magnesium sulfate. The solvent is then distilled off and isopropyl ether is added to the residue. The thus-obtained white powder is collected by filtration, washed with isopropyl ether and dried to give 2.1 g of the title compound.

IR(KBr)cm⁻¹: 1775, 1760, 1675, 1640.
NMR(CDCl₃, 90 MHz)δ: 0.90(t, J=6 Hz, 3H), 0.93(d, J=6 Hz, 3H), 1.00–1.80(m, 3H), 1.58 & 1.60(each d, J=6 Hz, 3H), 2.26(s, 6H), 2.76(t, J=6 Hz, 2H), 3.50(s, 2H), 3.72(m, 2H), 4.00 & 4.03(each d, J=6 Hz, 2H), 4.26 & 4.50(ABq, J=13.5 Hz, 2H), 4.33 (t, J=6 Hz, 2H), 4.93 & 4.96(each d, J=4.5 Hz, 1H), 5.42(b-s, 2H), 5.86(m, 1H), 6.26(s, 1H), 6.94(m, 1H), 8.00 & 8.06(each d, J=9 Hz, 1H).

Elemental analysis for C₂₆H₃₇N₉O₇S₃
Calcd.(%): C, 45.67; H, 5.45; N, 18.43; Found (%): C, 45.70; H, 5.58; N, 18.52.

EXAMPLE 2

1-(3-Methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Using 1-iodoethyl 3-methylbutyl carbonate produced by the procedure of Reference Example 2 and following the procedure of Example 1, the title compound is obtained.

IR(KBr)cm⁻¹: 1780, 1765, 1675, 1620.
NMR(CDCl₃, 90 MHz)δ: 0.90(d, J=6 Hz, 6H), 1.20–1.90 (m, 3H), 1.56 & 1.60(each d, J=6 Hz, 3H), 2.24(s, 6H), 2.75(t, J=6 Hz, 2H), 3.50(s, 2H), 3.72(m, 2H), 4.20(t, J=6 Hz, 2H), 4.26 & 4.50(ABq, J=13.5 Hz, 2H), 4.32(t, J=6 Hz, 2H), 4.92 & 4.95(each d, J=4.5 Hz, 1H), 5.38(b-s, 2H), 5.80(m, 1H), 6.25 (s, 1H), 6.95(m, 1H), 7.85 & 8.05(each d, J=9 Hz, 1H).

Elemental analysis for C₂₆H₃₇N₉O₇S₃
Calcd.(%): C, 45.67; H, 5.45; N, 18.43; Found (%): C, 45.59; H, 5.40; N, 18.56.

EXAMPLE 3

1-(3-Methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride In 40 ml of dichloromethane is dissolved 3 g of the compound produced by the procedure of Example 2, and to the solution is added 5 ml of 3.78N hydrochloric acid-ethyl ether with ice-cooling. The white solid is collected by filtration, washed with ethyl ether and dried under reduced pressure to give 2.8 g of the title compound.

IR(KBr)cm⁻¹: 1765, 1680, 1630.
NMR(D₂O, 60 MHz)δ: 0.94(d, J=6 Hz, 6H), 1.2–2.0(m, 6H), 3.12(s, 6H), 3.6–5.0(m, 12H), 5.18(d, J=4.5 Hz, 1H), 5.70(d, J=4.5 Hz, 1H), 6.7(s, 1H), 6.82(m, 1H).

Elemental analysis for C₂₆H₃₇N₉O₇S₃.2HCl.2H₂O
Calcd.(%): C, 39.39; H, 5.47; N, 15.90; Found (%): C, 39.52; H, 5.43; N, 15.79.

EXAMPLE 4

1-(2-Ethylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Using 1-iodoethyl 2-ethylbutyl carbonate produced from 1-chloroethyl 2-ethylbutyl carbonate by the procedure of Reference Example 2(b) and following the procedure of Example 1, the title compound is obtained.

IR(KBr)cm$^{-1}$: 1775, 1760, 1675, 1640.

NMR(CDCl$_3$, 90 MHz)δ: 0.90(t, J=6 Hz, 6H), 1.10–1.80 (m, 5H), 1.58 & 1.61(each d, J=6 Hz, 3H), 2.26(s, 6H), 2.76(t, J=6 Hz, 2H), 3.50(s, 2H), 3.70(m, 2H), 4.12(d, J=5 Hz, 2H), 4.26 & 4.50(ABq, J=13.5 Hz, 2H), 4.33(t, J=6 Hz, 2H), 4.93 & 4.96(each d, J=4.5 Hz, 1H), 5.40(b-s, 2H), 5.90(m, 1H), 6.26(s, 1H), 6.98(m, 1H), 8.02 & 8.08(each d, J=9 Hz, 1H).

Elemental analysis for $C_{27}H_{39}N_9O_7S_3$

Calcd.(%): C, 46.47; H, 5.63; N, 18.06; Found (%): C, 46.35, H, 5.68; N, 18.01.

EXAMPLE 5

1-(2-Methylpropyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Using 1-iodoethyl 2-methylpropyl carbonate produced from 1-chloroethyl 2-methylpropyl carbonate by the procedure of Reference Example 2(b) and following the procedure of Example 1, the title compound is obtained.

IR(KBr)cm$^{-1}$: 1775, 1680, 1640.

NMR(CDCl$_3$, 90 MHz)δ: 0.93(d, J=6 Hz, 6H), 1.56 & 1.60(each d, J=6 Hz, 3H), 1.70–2.25(m, 1H), 2.26(s, 6H), 2.76(t, J=6 Hz, 2H), 3.50(s, 2H), 3.70(m, 2H), 3.96(d, J=6 Hz, 2H), 4.26 & 4.50 (ABq, J=13.5 Hz, 2H), 4.33(t, J=6 Hz, 2H), 4.94 & 4.96(each d, J=4.5 Hz, 1H), 5.40(b-s, 2H), 5.86 (m, 1H), 6.26(s, 1H), 6.90(m, 1H), 8.02 & 8.08 (each d, J=9 Hz, 1H).

Elemental analysis for $C_{25}H_{35}N_9O_7S_3$

Calcd.(%): C, 44.83; H, 5.27; N, 18.82; Found (%): C, 44.56; H, 5.36; N, 18.52.

EXAMPLE 6

1-(2-Methylpentyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Using 1-iodoethyl 2-methylpentyl carbonate produced from 1-chloroethyl 2-methylpentyl carbonate by the procedure of Reference Example 2(b) and following the procedure of Example 1, the title compound is obtained.

IR(KBr)cm$^{-1}$: 1775, 1680, 1620.

NMR(CDCl$_3$, 90 MHz)δ: 0.90(t, J=6 Hz, 3H), 0.93(d, J=6 Hz, 3H), 1.0–2.0(m, 5H), 1.59 & 1.63(each d, J=6 Hz, 3H), 2.26(s, 6H), 2.78(t, J=6 Hz, 2H), 3.51(s, 2H), 3.70(m, 2H), 4.03(m, 2H), 4.26 & 4.50(ABq, J=13.5 Hz, 2H), 4.33(t, J=6 Hz, 2H), 4.93 & 4.96(each d, J=4.5 Hz, 1H), 5.40(b-s, 2H), 5.90(m, 1H), 6.26(s, 1H), 6.96(m, 1H), 8.03 & 8.08(each d, J=9 Hz, 1H).

Elemental analysis for $C_{27}H_{39}N_9O_7S_3$

Calcd.(%): C, 46.47; H, 5.63; N, 18.06; found (%): C, 46.24; H, 5.73; N, 17.95.

EXAMPLE 7

1-(2,2-Dimethylpropoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Using 1-iodoethyl 2,2-dimethylpropyl carbonate produced from 1-chloroethyl 2,2-dimethylpropyl carbonate by the procedure of Reference Example 2(b) and following the procedure of Example 1, the title compound is obtained.

IR(KBr)cm$^{-1}$: 1780, 1760, 1680, 1645, 1620.

NMR(CDCl$_3$, 90 MHz)δ: 0.94(s, 9H), 1.58 & 1.62 (each d, J=6 Hz, 3H), 2.26(s, 6H), 2.76(t, J=6 Hz, 2H), 3.51(s, 2H), 3.72(m, 2H), 3.86(s, 2H), 4.28 & 4.50(ABq, J=13.5 Hz, 2H), 4.33(t, J=6 Hz, 2H), 4.93 & 4.96(each d, J=4.5 Hz, 1H), 5.33(b-s, 2H), 5.86(m, 1H), 6.26(s, 1H), 6.96(m, 1H), 8.00 & 8.06(each d, J=9 Hz, 1H).

Elemental analysis for $C_{26}H_{37}N_9O_7S_3$

Calcd.(%): C, 45.67; H, 5.45; N, 18.43; Found (%): C, 45.57; H, 5.47; N, 18.15.

EXAMPLE 8

1-(1-Methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Using 1-iodoethyl 2-pentyl carbonate produced from 1-chloroethyl 2-pentyl carbonate by the procedure of Reference Example 2(b) and following the procedure of Example 1, the title compound is obtained.

IR(KBr)cm$^{-1}$: 1780, 1760, 1675, 1630.

NMR(CDCl$_3$, 90 MHz)δ: 0.90(t, J=6 Hz, 3H), 1.0–1.8 (m, 5H), 1.28(d, J=6 Hz, 3H), 1.58 & 1.62(each d, J=6 Hz, 3H), 2.26(s, 6H), 2.76(t, J=6 Hz, 2H), 3.50(s, 2H), 3.72(m, 2H), 4.26 & 4.50(ABq, J=13.5 Hz, 2H), 4.33(t, J=6 Hz, 2H), 4.65–5.05 (m, 1H), 4.93 & 4.96(each d, J=4.5 Hz, 1H), 5.43 (b-s, 2H), 5.86(m, 1H), 6.26(s, 1H), 6.95(m, 1H), 8.00 & 8.08(each d, J=9 Hz, 1H).

Elemental analysis for $C_{26}H_{37}N_9O_7S_3$

Calcd.(%): C, 45.67; H, 5.45; N, 18.43; Found (%): C, 45.66; H, 5.37; N, 18.50.

EXAMPLE 9

1-(3-Methyl-3-butenyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Using 1-iodoethyl 3-methyl-3-butenyl carbonate produced from 1-chloroethyl 3-methyl-3-butenyl carbonate by the procedure of Reference Example 2(b) and following the procedure of Example 1, the title compound is obtained.

IR(KBr)cm$^{-1}$: 1780, 1680, 1645.

NMR(CDCl$_3$, 90 MHz)δ: 1.58 & 1.62(each d, J=6 Hz, 3H), 1.76(s, 3H), 2.26(s, 6H), 2.4(t, J=6 Hz, 2H), 2.78 (t, J=6 Hz, 2H), 3.5(s, 2H), 3.72(m, 2H), 4.15–4.56(m, 6H), 4.8(m, 2H), 4.93 & 4.96(each d, J=4.5 Hz, 1H), 5.4(b-s, 2H), 5.88(m, 1H), 6.28(s, 1H), 6.98(m, 1H), 8.02 & 8.08(each d, J=9 Hz, 1H).

Elemental analysis for $C_{26}H_{35}N_9O_7S_3$

Calcd.(%): C, 45.80; H, 5.17; N, 18.49; Found (%): C, 45.71; H, 5.10; N, 18.57.

EXAMPLE 10

1-(Pentyloxycarbonyloxy)ethyl 7β-[2-(2-aiminothiazol-4-yl)acetamido]-3-[[[1-(2-dimethylaminoethyl)-1H-tetrazol-5-yl]thio]methyl]ceph-3-em-4-carboxylate Using 1-iodoethyl pentyl carbonate produced from 1-chloroethyl pentyl carbonate by the procedure of Reference Example 2(b) and following the procedure of Example 1, the title compound is obtained.

IR(KBr)cm$^{-1}$: 1780, 1760, 1680, 1645, 1620

NMR(CDCl$_3$, 90 MHz)δ: 0.9(t, J=6 Hz, 3H), 1.0-1.85 (m, 6H), 1.56 & 1.60(each d, J=6 Hz, 3H), 2.26 (s, 6H), 2.76(t, J=6 Hz, 2H), 3.50(s, 2H), 3.70 (m, 2H), 4.17(t, J=6 Hz, 2H), 4.26 & 4.50(ABq, J=13.5 Hz, 2H), 4.33(t, J=6 Hz, 2H), 4.93 & 4.96 (each d, J=4.5 Hz, 1H), 5.50(b-s, 2H), 5.86(m, 1H), 6.26(s, 1H), 6.92(m, 1H), 8.02 & 8.08 (each d, J=9 Hz, 1H).

Elemental analysis for C$_{26}$H$_{37}$N$_9$O$_7$S$_3$.0.1C$_6$H$_{14}$O

Calcd.(%): C, 46.03; H, 5.58; N, 18.16; Found (%): C, 46.02; H, 5.52; N, 18.17.

EXAMPLE 11

1-(2,4-Dimethyl-3-pentyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate A mixture of 1.78 g of 1-chloroethyl 2,4-dimethyl-3-pentyl carbonate and 5 g of sodium iodide is stirred in 30 ml of acetonitrile at 70° C. for 4 hours and concentrated. The residue is extracted with ether and concentrated to give crude 1-iodoethyl 2,4-dimethyl-3-pentyl carbonate. In 30 ml of dimethylformamide is dissolved 3.6 g of potassium 7β-[2-(2-aminothiazol-4-yl)acetamido]-3-[[[1-(2-dimethylaminoethyl)-1H-tetrazol-5-yl]thio]methyl]-ceph-3-em-4-carboxylate, and with ice-cooling and stirring, the above 1-iodoethyl 2,4-dimethyl-3-pentyl carbonate is added thereto at one stroke, followed by stirring for 5 minutes. The reaction mixture is poured into a mixture of 150 ml of ethyl acetate and 150 ml of ice-cooled 20% aqueous sodium chloride. The organic layer is separated, washed with two 150-ml portions of saturated aqueous sodium chloride and extracted with 40 ml of 1N hydrochloric acid. The extract is subjected to column chromatography using Diaion MCI ® GEL CHP-20P (Mitsubishi Chemical Industries Limited, Japan), elution being carried out with acetonitrile-0.01N hydrochloric acid. The fractions containing the desired product are combined and lyophilized to give 940 mg of the title compound as a white powder.

IR(KBr)cm$^{-1}$: 1785, 1760, 1690, 1630.

NMR(DMSO-d$_6$, 90 MHz)δ: 0.84 & 0.88(each d, 12H), 1.53 & 1.57(each d, 3H), 1.6-2.2(m, 2H), 1.84 (s, 6H), 3.65(s, 2H), 3.66(t, J=6 Hz, 2H), 3.73 & 3.91(ABq, J=18 Hz, 2H), 4.32(t, J=6 Hz, 2H), 4.32 & 4.54(ABq, J=13 Hz, 2H), 4.80(t, J=6 Hz, 2H), 5.14(d, J=5 Hz, 1H), 5.71(m, 1H), 6.65(s, 1H) 6.82(m, 1H), 9.23 & 9.26(each d, J=8 Hz, 1H), 9.3(b, 2H), 11.5(b, 1H).

Elemental analysis for C$_{28}$H$_{41}$N$_9$O$_7$S$_3$.2HCl.2.5H$_2$O

Calcd. (%): C, 40.53; H, 5.83; N, 15.19; Found (%): C, 40.57; H, 5.90; N, 15.38.

EXAMPLE 12

1-(3-Pentyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate Following the same procedure as Example 11, the title compound is obtained.

IR(KBr)cm$^{-1}$: 1780, 1760, 1680, 1630.

NMR(DMSO-d$_6$, 90 MHz)δ: 0.86(t, J=7 Hz, 6H), 1.2-1.9(m, 4H), 1.51 & 1.55(each d, J=6 Hz, 3H), 2.84(s, 6H), 3.64(s, 2H), 3.64(t, J=6 Hz, 2H), 3.72 & 3.92(ABq, J=18 Hz, 2H), 4.26 & 4.55(ABq, J=13 Hz, 2H), 4.55 & 4.58(each d, J=6 Hz, 1H), 4.80(t, J=6 Hz, 2H), 5.13 & 5.16(each d, J=5 Hz, 1H), 5.73(m, 1H), 6.66(s, 1H), 6.85 (m, 1H), 9.24 & 9.28(each d, J=8 Hz, 1H), 9.3(b, 2H), 11.6(b, 1H).

Elemental analysis for C$_{26}$H$_{37}$N$_9$O$_7$S$_3$.2HCl.1.5H$_2$O

Calcd. (%): C, 39.84; H, 5.40; N, 16.08; Found (%): C, 40.09; H, 5.49; N, 15.84.

EXAMPLE 13

1-(1-Methylbutyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate (a) Production of 1-(1-methylbutoxycarbonyloxy)ethyl 7β-amino-3-[[[1-(2-dimethylaminoethyl)-1H-tetrazol-5-yl]-thio]methyl]ceph-3-em-4-carboxylate dihydrochloride.

To 180 ml of dimethylformamide solution containing 12.66 g of 7β-amino-3-[[[1-(2-dimethylaminoethyl)-1H-tetrazol-5-yl]thio]methyl]ceph-3-em-4-carboxylate dihydrochloride is added 5.88 g of potassium acetate. The solution is cooled to −5° C. With stirring, 17.1 g of 1-iodoethyl 2-n-pentyl carbonate is added at one stroke, followed by stirring for 5 minutes. The reaction mixture is poured into a mixture of 240 ml of methylene chloride and 240 ml of 0.1N-hydrochloric acid and the aqueous layer is separated. The aqueous layer is adjusted to pH 6.0 with a saturated aqueous solution bicarbonate solution and extracted twice with 240 ml each portion of methylene chloride. To the methylene chloride solution is added 450 ml of water and the aqueous solution is adjusted to pH 2.0 with 4N-hydrochloric acid. The aqueous layer is separated and methylene chloride contained in the aqueous solution is removed under reduced pressure. Then, the aqueous layer is lyophilized to obtain 7.8 g of the title compound.

IR(KBr)cm$^{-1}$: 1780, 1755.

(b) Production of 1-(1-methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]-ceph-3-em-4-carboxylate To a mixture of 40 ml of water and 40 ml of methylene chloride is added 2.47 g of the compound obtained in the above (a), followed by addition of 0.75 g of sodium bicarbonate with stirring. The organic layer is separated and dried over anhydrous magnesium sulfate. After the drying agent is removed by filtration, to the filtrate is added 25 ml of dimethylformamide solution containing 0.80 g of 2-(2-aminothiazol-4-yl)acetic acid hydrochloride and 0.83 g of dicyclohexylcarbodiimide, followed by stirring at room temperature to cause precipitation. The precipitates are removed by filtration. To the filtrate are added 200 ml of ethyl acetate and 150 ml of ice water and the organic layer is separated, washed with 150 ml of water and 150 ml of saturated aqueous sodium chloride and then dried over anhydrous magnesium sulfate. The solvent is distilled off under reduced pressure. To the residue is added isopropyl ether and the resultant precipitate is collected by filtration and dried to obtain 0.43 g of white powder.

This product shows the same IR and NMR spectra as those of the product obtained in Example 8.

EXAMPLE 14

1-(1-Methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate To a mixture of 50 ml of water and 75 ml of methylene chloride is added 3.08 g of 1-(1-methylbutoxycarbonyloxy)ethyl 7β-amino-3-[[[1-(2-dimethylaminoethyl)-1H-tetrazol-5-yl]thio]methyl]ceph-3-em-4-carboxylate dihydrochloride obtained in Example 13(a) and the mixture is stirred together with 0.84 g of sodium bicarbonate. The organic layer is separated and dried over anhydrous magnesium sulfate. The solvent is distilled off under reduced pressure and the residue is dissolved in 75 ml of methylene chloride and cooled to −25° C. To this solution is added a solution of 1.5 g of 4-chloroacetoacetyl chloride in 3.5 ml of methylene chloride and the mixture is stirred at −20° C.−−15° C. for 15 minutes. Then, 1.9 g of thiourea and 25 ml of dimethylacetamide are added thereto, followed by stirring at room temperature for 3 hours. Water is added to the reaction mixture and the aqueous layer is separated, adjusted to pH 6.0 and extracted with methylene chloride. The organic layer is washed with water and then dried over anhydrous magnesium sulfate. The solvent is distilled off under reduced pressure and isopropyl ether is added to the residue. The resultant precipitates are collected by filtration and dried to obtain 2.2 g of the title compound.

This product shows the same IR and NMR spectra as those of the product obtained in Example 8.

EXAMPLE 15

1-(1-Methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate (a) Production of 1-(1-methylbutoxycarbonyloxy)ethyl 7β-[2-(2-aminothiazol-4-yl)acetamido]-3-acetoacetoxymethylceph-3-em-4-carboxylate In 50 ml of dimethylacetamide is dissolved 4.76 g of sodium 7β-[2-(2-aminothiazol-4-yl)acetamido]-3-acetoacetoxymethylceph-3-em-4-carboxylate and the solution is cooled to −5° C. With stirring, 5.7 g of 1-iodoethyl 2-n-pentyl carbonate is added at one stroke, followed by sitrring for further 5 minutes. The reaction mixture is poured into a mixture of 300 ml of ethylacetate and 200 ml of ice-water and the organic layer is separated. The aqueous layer is extracted with 200 ml of ethyl acetate and these organic layers are combined, washed with 150 ml each portion of ice water (three times) and 150 ml portions of saturated aqueous sodium chloride (three times) in that order and dried over anhydrous magnesium sulfate. The solvent is then distilled off under reduced pressure and isopropyl ether is added to the residue. The resultant white powder is collected by filtration, washed with isopropyl ether and then dried to obtain 3.8 g of the title compound.

IR(KBr)cm$^{-1}$: 1780, 1750, 1680.

NMR(CDCl$_3$, 90 MHz)δ: 0.90(t, J=6 Hz, 3H), 1.0–1.8(m, 5H), 1.28(d, J=6 Hz, 3H), 1.58 & 1.62 (each d, J=6 Hz, 3H), 2.19(s, 3H), 3.42 & 3.65 (ABq, J=18 Hz, 2H), 3.50(s, 2H), 3.60(s, 2H), 3.72(m, 2H), 4.65–5.05 (m, 1H), 4.93 & 4.96(each d, J=4.5 Hz, 1H), 5.43 (b-s, 2H), 5.86(m, 1H), 6.26(s, 1H), 6.95(m, 1H), 8.00 & 8.08(each d, J=9 Hz, 1H).

(b) Production of 1-(1-methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.

To 45 ml of an acetone solution containing 3.5 g of the compound obtained in the above (a) is added 15 ml of an aqueous solution containing 1.35 g of 1-(2-dimethylaminoethyl)-5-mercapto-1H-tetrazole and 1.2 g of sodium bicarbonate. The mixture is heated to 40° C. for 1 hour with stirring. The reaction mixture is poured into a mixture of 230 ml of ethyl acetate and 80 ml of ice water and the organic layer is separated and then washed with ice water and saturated aqueous sodium chloride and dried over anhydrous magnesium sulfate. Then, the solvent is distilled off under reduced pressure. The residue is dissolved in a small amount of acetone and insoluble matter is removed by filtration. Isopropyl ether is added to the filtrate and resulting precipitates are collected by filtration to obtain 0.09 g of the title compound as white powder.

This product shows the same IR and NMR spectra as those of the product obtained in Example 8.

FORMULATION EXAMPLE 326 g of 1-(1-methylbutoxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate (250 g in terms of 7β-[2-(2-aminothiazol-4-yl)acetamido]-3-[[[1-(2-dimethylaminoethyl)-1H-tetrazol-5-yl]thio]methyl]ceph-3-em-4-carboxylic acid, i.e., non-ester compound), 37 g of crystalline cellulose (Avicel ®), 357 g of tartaric acid and 2.0 g of magnesium stearate are homogeneously mixed. From the mixture, a slug is produced by a slug tablet machine. The slug is made into granules, which are mixed with 3.5 g of magnesium stearate and 16.5 g of crystalline cellulose as lubricants. Tablets containing 370 mg of the mixture per one tablet (125 mg in terms of non-ester compound) are produced.

EXPERIMENTAL EXAMPLE

The compounds of Examples 2, 4, 6, 7 and 8 and the 1-(ethoxycarbonyloxy)ethyl ester of compound [II] (briefly, compound A) are each administered orally to a mouse in a dose of 100 mg/kg in terms of non-ester compound, i.e., compound [II]. At 0.25, 0.5, 1.0 and 2.0 hours after administration, the concentration of the non-ester compound in the mouse plasma is determined by the cup assay using *Proteus mirabilis* Eb313 as the test organism and the area under the concentration-time curve for 0–2 hours (AUC) is calculated.

As control, the non-ester compound is administered subcutaneously to a mouse and the AUC value is similarly calculated.

The bioavailability defined in the following formula is shown in the Table 1.

$$\text{Bioavailability (\%)} = \frac{AUC(\text{oral administration})}{AUC(\text{subcutaneous administration})} \times 100$$

TABLE 1

| Test compound (Example No.) | Plasma level of non-ester compound (μg/ml) n = 3* (hr) | | | | AUC μg·hr/ml | Bio-availability (%) |
|---|---|---|---|---|---|---|
| | 0.25 | 0.5 | 1 | 2 | | |
| 2 | 65.8 | 28.6 | 9.66 | 1.68 | 35.3 | 90.8 |
| 4 | 43.9 | 39.5 | 8.73 | 0.22 | 32.4 | 83.6 |
| 6 | 50.2 | 31.0 | 7.31 | 2.86 | 31.1 | 80.1 |
| 7 | 65.7 | 34.5 | 7.23 | 1.86 | 35.7 | 92.0 |
| 8 | 62.7 | 48.9 | 11.2 | 0.86 | 42.5 | 110.6 |
| Compound A | 14.7 | 9.2 | 2.4 | 0.7 | 9.28 | 23.9 |
| Control subcutaneous administration of non-ester compound | 69.2 | 29.0 | 13.2 | 1.5 | 38.8 | 100 |

*Average for 3 mice

What is claimed is:

1. A compound namely, being 1-(3-methylbutoxycarbonyloxy)ethyl 7β-[2-(2-aminothiazol-4yl)acetamido]-3-[[[1-(2-dimethylaminoethyl)-1H-tetrazol-5-yl]thio]-methyl]ceph-3-em-4-carboxylate.

2. A compound namely, 1-(2,2-dimethylpropoxycarbonyloxy)ethyl 7β-[2-(2-aminothiazol-4-yl)acetamido]-3-[[[1-(2-dimethylaminoethyl)-1H-tetrazol-5-yl]thio]-methyl]ceph-3-em-4-carboxylate.

3. A compound namely, 1-(1-methylbutoxycarbonyloxy)ethyl 7β-[2-(2-aminothiazol-4-yl)acetamido]-3-[[[1-(2-dimethylaminoethyl)-1H-tetrazol-5-yl]thio]-methyl]ceph-3-em-4-carboxylate.

* * * * *